United States Patent [19]

Weaver et al.

[11] 4,265,812
[45] May 5, 1981

[54] AZO DYES DERIVED FROM 3-AMINO-2,1-BENZISOTHIAZOLES AND AROMATIC AMINE COUPLERS CONTAINING SULFO GROUPS, OR SALTS THEREOF

[75] Inventors: Max A. Weaver; Clarence A. Coates, Jr.; Jean C. Fleischer, all of Kingsport, Tenn.

[73] Assignee: Eastman Kodak Company, Rochester, N.Y.

[21] Appl. No.: 44,439

[22] Filed: Jun. 1, 1979

[51] Int. Cl.³ ..................... C09B 29/22; C09B 62/08
[52] U.S. Cl. ..................................... 260/158; 260/155
[58] Field of Search ............................... 260/158, 155

[56] References Cited

U.S. PATENT DOCUMENTS

| | | | |
|---|---|---|---|
| 3,761,462 | 9/1973 | Moritz | 260/158 |
| 3,870,696 | 3/1975 | Feeman | 260/158 |
| 4,052,379 | 10/1977 | Gourley | 260/158 |
| 4,063,881 | 12/1977 | Razavi | 260/158 |

Primary Examiner—John F. Niebling
Attorney, Agent, or Firm—Donald W. Spurrell; Daniel B. Reece, III

[57] ABSTRACT

Disclosed are mono azo dyes derived from diazotized 3-amino-2,1-benzisothiazoles and certain aniline, 1,2,3,4-tetrahydroquinoline, and benzomorpholine couplers containing sulfoalkyl groups. These dyes impart fast violet to blue shades on polyamide fibers and have the general formula

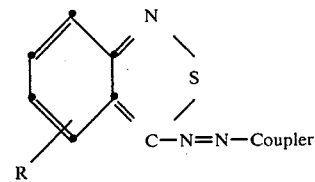

wherein the Coupler is a derivative of an aniline, tetrahydroquinoline, or benzomorpholine derivative wherein a $-Z-SO_3M$ group is attached to the nitrogen thereof, R may be hydrogen or one to three substituents such as lower alkyl, lower alkoxy, chlorine, bromine, iodine, sulfamoyl, and substituted sulfamoyl, the coupler ring may contain one or more substituents selected from lower alkyl, lower alkoxy, halogen, acylamido, alkylthio or aryloxy, the remaining hydrogen of the aniline coupler nitrogen may be replaced by a substituent such as lower alkyl, substituted lower alkyl, lower alkenyl, aryl, or cycloalkyl, M is $Na^+$, $K^+$, $NH_4^+$, and Z is a linking group such as ethylene.

6 Claims, No Drawings

AZO DYES DERIVED FROM 3-AMINO-2,1-BENZISOTHIAZOLES AND AROMATIC AMINE COUPLERS CONTAINING SULFO GROUPS, OR SALTS THEREOF

This invention concerns mono azo dyes derived from diazotized 3-amino-2,1-benzisothiazoles and certain aniline, 1,2,3,4-tetrahydroquinoline, and benzomorpholine couplers containing sulfoalkyl groups. These dyes are useful for dyeing synthetic fibers, cellulose acetate and wool, and impart fast violet to blue shades on polyamide fibers. The dyes, in general, exhibit improved properties such as fastness to light, sublimation, ozone, gas, perspiration, crock, and wash, and exhibit excellent build, pH stability, bloom resistance, depth of shade, levelling, migration, and the like.

The dyes of this invention have the general formula:

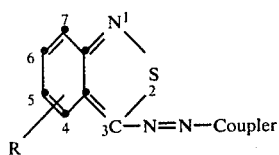

wherein the Coupler is of the formulae

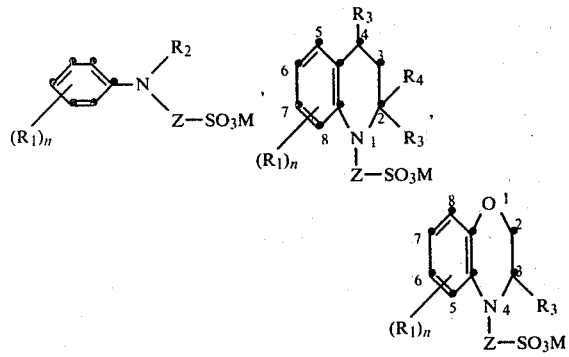

wherein R may be hydrogen or one to three substituents selected from lower alkyl, lower alkoxy, chlorine, bromine, iodine, lower alkylsulfonyl, sulfamoyl, and sulfamoyl substituted with lower alkyl; $R_1$ is selected from hydrogen, lower alkyl, aryl, alkylamino, 2-furyl, halogen, lower alkoxy, aryloxy, and —NHCO—$R_5$ and —NHSO$_2$—$R_5$ wherein $R_5$ is selected from lower alkyl which may be substituted with hydroxy, lower alkoxy, cyano, aryloxy, aryl, halogen, cycloalkyl, lower alkylcarbonyloxy, or carbamoyl; $R_2$ is selected from hydrogen, aryl, cycloalkyl, and lower alkyl which may be substituted with lower alkoxy, lower alkoxyalkoxy, aryl, cycloalkyl, lower alkylcycloalkyl, 2-furyl, NHCOR$_5$, NHSO$_2$R$_5$, aryloxy, alkylcarbonyl, carbamoyl, lower alkyl carbamoyl, lower alkyl substituted carbamoyl, cyano, alkanoyloxy, halogen, alkoxycarbonyl, succinimido, glutarimido, phthalimido, 2-pyrrolidono, sulfamoyl, lower alkyl substituted sulfamoyl, lower alkylsulfonamido, NHSO$_2$-aryl, NHCOO-alkyl, NHCONH-alkyl, formamido, alkylsulfonyl, arylsulfonyl, alkylthio, arylthio or SO$_3$M; $R_2$ may in conjunction with $R_1$ form a 1,2,3,4-tetrahydroquinoline or benzomorpholine derivative; n is 0, 1 or 2; M is Na$^+$, K$^+$, NH$_4^+$, or H$^+$; $R_3$ and $R_4$ are each selected from hydrogen or lower alkyl; Z is selected from straight or branched chain lower alkylene, lower alkylene substituted with aryl, aryloxy, alkoxy, halogen, aryloxy or SO$_3$M, —CH$_2$(CH$_2$)$_m$—X—CH$_2$(CH$_2$)$_p$, where m is 1, 2, or 3, p is 0, 1, 2, or 3, and X is O, S, SO$_2$,

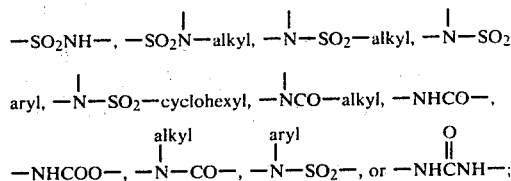

and the various aryl groups may be substituted with lower alkyl, lower alkoxy, or halogen. The term "lower" as used herein, means 1-6 carbons.

The intermediate couplers containing a sulfoethyl group may be prepared in the best purity by reacting aromatic amines such as anilines, tetrahydroquinolines and benzomorpholines with vinylsulfonyl fluoride, followed by basic hydrolysis. Typical is the reaction

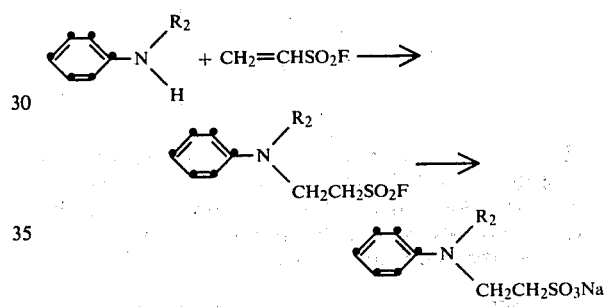

Other general methods useful for preparing these couplers containing sulfo groups are given by R. B. Wagner and H. D. Zook, "Synthetic Organic Chemistry", John Wiley & Sons, Inc., New York, 1953, pp. 812–819. Exemplary are the methods (I) oxidation of mercaptans; (II) alkylation of alkali sulfite; and (III) addition of bisulfites to unsaturated compounds, as follows:

 (I);

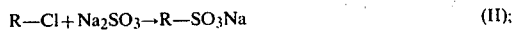 (II);

 (III).

The following coupler intermediates, bearing one or more halogens, are typical of those appropriate for reacting with sodium sulfite according to above method II.

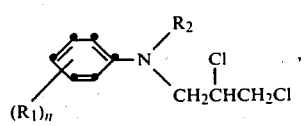

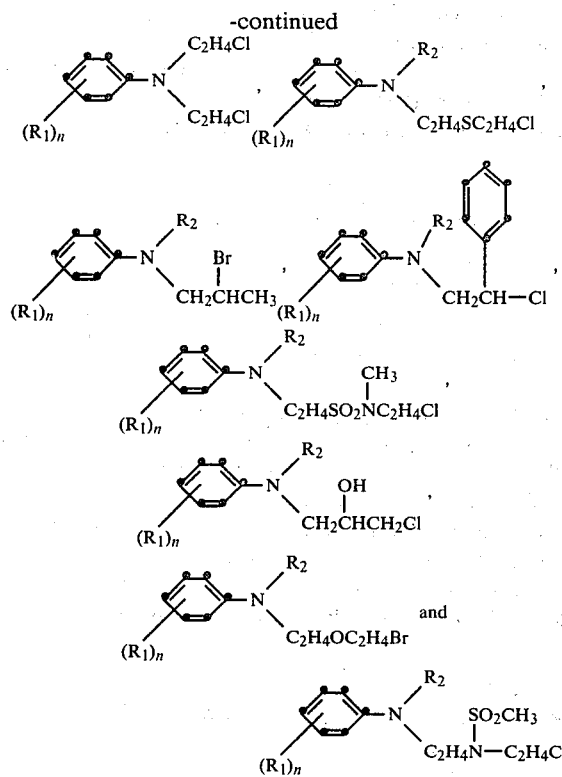

The halogen containing couplers are in general prepared by reacting the corresponding known hydroxy compounds with POCl₃, SOCl₂, POBr₃, PBr₃, and the like by methods well known in the art. The tetrahydroquinolines and benzomorpholines are similarly prepared.

The following coupler intermediates are typical of those containing vinyl groups capable of being reacted with sodium bisulfite method III as disclosed, for example, in U.S. Pat. Nos. 3,369,013; 3,415,810; and 3,472,833.

and vinylsulfonyl fluoride, respectively by methods well known in the art.

Preparation of
N-(2-Fluorosulfonylethyl)-N-ethyl-m-toluidine

N-Ethyl-m-toluidine (66.5 g) (0.5 m) is dissolved in isopropyl alcohol (75 ml) and vinylsulfonyl fluoride (55 g, 0.5 m) is added dropwise over 1.25 hr. The reaction exotherms to 38° C. and the reaction mixture is stirred for 1 hr. at ambient temperature and drowned into 500 ml of ice and water. The product is collected by filtration, washed with water, and dried in air. The product melts at 32°–34° C.

Preparation of
N-(2-Potassiosulfoethyl)-N-ethyl-m-toluidine

N-(2-Fluorosulfonylethyl)-N-ethyl-m-toluidine (24.5 g, 0.1 m) is stirred in water (200 ml) and potassium hydroxide (10 g) for 1–3 hours at room temperature or until thin-layer chromatography shows the reaction to be complete. The product is not isolated but is used as an aqueous solution in the coupling reaction.

Preparation of
N-(2-Fluorosulfonylethyl)-N-ethylaniline

N-Ethylaniline (48.4 g 0.4 m), triethylamine (40.4 g 0.4 m) and benzene (100 ml) are stirred together at room temperature and 2-chloroethanesulfonyl fluoride (58.6 g, 0.4 m) is added dropwise. The reaction mixture is heated at reflux for 1.5 hr. after the addition is completed. The reaction mixture is cooled and filtered to remove any insoluble salts, and the benzene is removed by distillation. The crude product is drowned into hexane (150 ml) and purified by filtration and washing with hexane. The product melts at 48°–50° C.

Preparation of N-(2-Potassiosulfoethyl)-N-ethylaniline

N-(2-Fluorosulfonylethyl)-N-ethylaniline (22.8 g, (0.1 m) is stirred in water (200 ml) and potassium hydroxide (10 g) for 1–3 hrs. or until thin-layer chromatography shows reaction to be complete. The product is not isolated but is used as an aqueous solution in the coupling reaction.

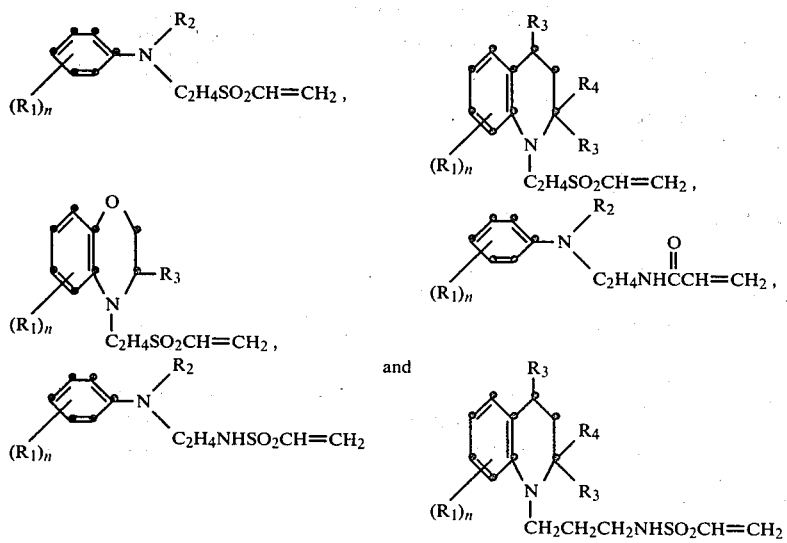

Intermediates containing the acrylamide and vinylsulfonamido groups can be prepared by reacting the corresponding amino compound with acryloyl chloride

Preparation of N-(2-Fluorosulfonylethyl)-2-methyl-5-acetamidoaniline

2-Methyl-5-acetamido aniline (49.2 g, 0.3 m), triethyl amine (32.7 g, 0.3 m) and p-dioxane (350 ml) are stirred together at room temperature. 2-Chloroethane sulfonylfluoride (43.0 g, 0.3 m) is added dropwise allowing temperature to rise to 45° C. The reaction mixture is then heated at reflux for 3 hrs. When thin-layer chromatography shows reaction to be complete, the reaction is allowed to cool and then drowned into water (2000 ml). The product is collected by filtration, washed with water and melts at 154°–155° C.

Preparation of N-(2-Potassiosulfoethyl)-2-methyl-5-acetamido aniline

N-(2-Fluorosulfonylethyl-2-methyl-5-acetamidoaniline (13.7 g, 0.05 m) is stirred with water (100 ml.) and potassium hydroxide (5.0 g) at room temperature for 2 hrs. when thin-layer chromatography shows reaction to be complete. The aqueous solution is used in the coupling reaction without further isolation.

Preparation of N-(2-Fluorosulfonylethyl)-2-methoxy-5-methylaniline

2-Methoxy-5-methylaniline (34.3 g 0.25 m) is dissolved in N,N-dimethylformamide (50 ml). Vinylsulfonyl fluoride (28.0 g, 0.26 m) is added dropwise at 20°–30° C. After the addition is complete the reaction mixture is allowed to stir at ambient temperature for 1 hr. The reaction is drowned into water (400 ml.), the product collected by filtration, washed with water and air dried. The product melts at 56°–58° C. The corresponding N-(2-potassiosulfoethyl)-2-methoxy-5-methylaniline is prepared therefrom by the above technique using KOH.

Preparation of N-(2-Fluorosulfonylethyl)-2,2,4,7-tetramethyl 1,2,3,4-tetrahydroquinoline 2,2,4,7-Tetramethyl-1,2,3,4-tetrahydroquinoline (94.5 g, 0.5 m) is dissolved in acetic acid (200 ml). The reaction is heated to 50° C. and vinylsulfonylfluoride (44.0 g, 0.5 m) added over 30 min. at 48°–50° C. The reaction is then stirred and heated for 2.5 hr. at 50°–55° C. Thin-layer chromatography shows the reaction to be complete. The reaction mixture is drowned into water (1200 ml), the product collected by filtration, washed with water and air dried. The product melts at 67°–69° C.

N-(2-fluorosulfonylethyl)-2,2,4-trimethyl-1,2,3,4-tetrahydroquinoline and N-(2-fluorosulfonylethyl 2,7-dimethyl-1,2,3,4-tetrahydroquinoline is prepared in same manner.

Preparation of N-(2-Sodiosulfoethyl)-2,2,4,7-tetramethyl-1,2,3,4-tetrahydroquinoline N-(2-fluorosulfonylethyl)-2,2,4,7-tetramethyl-1,2,3,4-tetrahydroquinoline (12.0 g, 0.04 m) is stirred with water (100 ml) and sodium hydroxide (5.0 g), warmed to 50° C. for 30 min., allowed to come to room temperature and stirred for 1.5 hr. Thin layer chromatography shows the reaction to be complete. The aqueous solution is not isolated but is used in the coupling reaction.

The same process is used to prepare N-(2-potassiosulfoethyl)-2,2,4-trimethyl-1,2,3,4-tetrahydroquinoline and N-(2-potassiosulfoethyl)-2,7-dimethyl-1,2,3,4-tetrahydroquinoline using KOH as the base.

Preparation of N-(2-Fluorosulfonylethyl)-3,6-dimethyl-2,3-dihydro-1,4-benzoxazine 3,6-Dimethyl-2,3-dihydro-1,4-benzoxazine (16.3 g, 0.1 m) is dissolved in acetic acid (40 ml) at ambient temperature and vinylsulfonylfluoride (11 g, 0.1 m) is added dropwise at 25°–35° C. After stirring for 1.5 hr., the reaction is complete. The reaction is drowned into water (400 ml). The dark oil which separates is extracted with hexane (1200 ml) and the hexane solution dried over sodium sulfate. The sodium sulfate is removed and the hexane distilled off to yield 23.3 g. of oily product. The N-2(potassiosulfoethyl)-3,6-dimethyl-2,3-dihydro-1,4-benzoxazine is prepared as above using KOH.

Preparation of N-(2-Fluorosulfonylethyl)-N-ethyl-m-acetamidoaniline

N-ethyl-m-acetamidoaniline (178.0 g, 1.0 m is dissolved in isopropyl alcohol (450 ml) and vinylsulfonylfluoride (110 g, 1.0 m) is added dropwise allowing temperature to rise to 40° C. The reaction is stirred for 2.5 hrs., the product collected by filtration, washed with cold ethanol and air dried.

Preparation of N-(2-Sodiosulfoethyl)-sulfonylethyl-N-ethyl-m-toluidine

N-(2-vinylsulfonylethyl-N-ethyl-m-toluidine (25.3 g, 0.1 m) in water solution (100 ml) is stirred with sodium bisulfite (11.0 g, 0.1 m). The reaction is heated to reflux and held for 15 min. The clear solution is drowned into ethanol (200 ml) and allowed to cool. The white solid is collected by filtration, air dried and melts at 237°–240° C.

Vinylsulfonyl fluoride may be prepared according to U.S. Pat. Nos. 2,653,973 and 2,884,452 and L. Z. Soboronskii, et. al., J. Gen. Chem. U.S.S.R., 28, 1913 (1958). The amine diazo precursors can be prepared from readily available intermediates by well known techniques.

This invention will be further illustrated by the following examples although it will be understood that these examples are included merely for purposes of illustration and are not intended to limit the scope of the invention.

EXAMPLES 1–10

To 25 ml. of concentrated $H_2SO_4$ is added 3.6 g. of $NaNO_2$ portionwise below 80° C. The solution is cooled and 50 ml. of 1:5 acid (1 part propionic acid:5 parts acetic acid) is added below 20° C. To the mixture is added 3-amino-2,1-benzisothiazole (7.5 g., 0.05 m) followed by 50 ml 1:5 acid, all at 0°–5° C. The reaction mixture is stirred at 0°–5° C. for 2 hrs.

Sufficient of the following couplers are added to 50 ml of water to give a 0.005 m solution of each.
N-Ethyl-N-2-sulfoethyl-m-toluidine, K salt (Example 1)
N-Ethyl-N-2-sulfoethyl-2-methoxy-5-methylaniline, K salt (Example 2)
5-Acetamido-2-methyl-N-2-sulfoethyl aniline, K salt (Example 3)
N-(2-Sulfoethyl)-1,2,3,4-tetrahydro-2,2,4,7-tetramethylquinoline, K salt (Example 4)
N-(2-Sulfoethyl)-1,2,3,4-tetrahydro-2,2,4-trimethylquinoline, K salt (Example 5)

2,7-Dimethyl-N-(2-sulfoethyl)-1,2,3,4-tetrahydroquinoline, K salt (Example 6)
8-Methoxy-5-methyl-N-(2-sulfoethyl)-1,2,3,4-tetrahydro quinoline, K salt (Example 7)
2,7-Dimethyl-N-(2,3-disulfopropyl)-1,2,3,4-tetrahydroquinoline, K salt (Example 8)
2,3-Dihydro-3,6-dimethyl-N-(2-sulfoethyl)-1,4-benzoxazine, K salt (Example 9)
2,3-Dihydro-3-methyl-7-methoxy-N-(2-sulfoethyl)-1,4-benzoxazine, K salt (Example 10)

To each chilled coupler solution is added a 0.005 M aliquot of the diazonium solution. The mineral acid is neutralized with potassium acetate and the coupling mixtures allowed to stand for 1 hr. Water is added to a total volume of 200–300 ml. and the dyes collected by filtration, washed with a 10% KCl water solution, and dried in air.

The dyes usually contain about an equal weight of dye and potassium sulfate and are used for example for dyeing polyamide fibers violet to blue shades without further purification. The dyes of the following tables are prepared in a similar manner. Neutralization using sodium hydroxide and ammonium hydroxide results in the corresponding sodium and ammonium salts of the dyes.

TABLE 1

[Structure: benzothiazole-C=N=N-phenyl with R, (R₁)ₙ, R₂, and Z—SO₃M substituents]

| R | (R₁)ₙ | R₂ | Z | M |
|---|---|---|---|---|
| H | 2-CH₃ | H | —CH₂CH₂— | K⁺ |
| " | 2-Cl | " | " | " |
| " | 2,5-di-Cl | " | " | " |
| " | 2,5-di-CH₃ | " | " | " |
| " | 2,5-di-OCH₃ | " | " | " |
| " | 3-OCH₃ | —C₂H₅ | " | " |
| " | 2-OCH₃ 5-NHCOCH₃ | H | " | " |
| " | 2-CH₃, 3-Cl | " | " | " |
| " | 2-OCH₃, 5-Cl | " | " | " |
| " | 3-NHCOCH₃ | —C₂H₅ | " | " |
| " | 3-NHCOC₂H₅ | —C₂H₄OCH₃ | " | " |
| " | 3-NHCOCH₂OH | —CH₂C₆H₅ | " | " |
| " | 3-NHCOCH₂OCH₃ | —C₆H₁₁ | " | " |
| " | 3-NHCOC₆H₅ | —CH₂C₆H₁₁ | " | " |
| " | 3-NHCOOC₂H₅ | —CH₂CH₂OC₆H₅ | " | " |
| " | 3-NHCONHC₂H₅ | —CH₂CH₂OH | " | " |
| " | 3-NHCOC₆H₁₁ | —CH₂CH(CH₃)₂ | " | " |
| " | 3-NHCOCH₂CN | —CH₂CH₂CH₂CH₃ | " | " |
| " | 3-NHCOCH₂OC₆H₅ | —CH₂CH₂OCOCH₃ | " | " |
| " | 3-NHCOCH₂C₆H₅ | —CH₂CH₂CONH₂ | " | " |
| " | 3-CH₃ | —CH₂CH₂NHCOCH₃ | " | " |
| " | " | —CH₂CH₂NHSO₂CH₃ | " | " |
| " | " | —CH₂CH₂SO₂NH₂ | " | " |
| " | " | —CH₂CH₂CH₂SO₂CH₃ | " | " |
| " | " | —CH₂CH₂SCH₃ | " | " |
| " | " | —CH₂CH₂N(COCH₂)₂ (pyrrolidine-dione) | —CH₂CH₂CH₂— | Na⁺ |
| " | " | —CH₂CH₂CH₂N(CO-CH₂)(CH₂CH₂) (piperidinone) | " | " |
| " | 3-OC₆H₅ | —CH₂CH₂N(CO)₂C₆H₄ (phthalimide) | " | NH₄⁺ |
| " | 3-CH₃ | —C₆H₅ | —CH₂CH₂— | Na⁺ |
| " | " | | —CH₂CH(CH₂OC₆H₅)— | " |
| " | " | —CH₂-furan(O) | | |
| " | " | —CH₂CH₂COOCH₃ | —CH₂CH(C₆H₅)— | " |
| " | " | —CH₂CH₂CN | —CH₂CH(CH₃)— | " |
| " | " | —C₂H₅ | —CH₂CH(OH)CH₂— | " |
| " | 2-CH₃S | H | —CH₂CH₂CH₂CH₂— | " |
| " | 3-CH₃ | —C₂H₄OC₂H₄OC₂H₅ | —CH₂CH(OCOCH₃)CH₂— | " |
| 5-Cl | " | —CH₂CH(OH)CH₂Cl | —CH₂CH₂— | " |
| " | 2-OCH₃, 5-CH₃ | | " | " |
| 5-Br | " | H | —CH₂CH₂OCH₂CH₂— | " |
| 5-I | " | H | " | " |

TABLE I-continued

| R | (R₁)ₙ | R₂ | Z | M |
|---|---|---|---|---|
| 6-Cl | " | " | —CH₂CH₂SO₂CH₂CH₂— | K⁺ |
| 6-CH₃ | 3-CH₃ | C₂H₅ | —CH₂CH₂SCH₂CH₂— | " |
| 6-OCH₃ | " | " | —CH₂CH₂N(SO₂CH₃)CH₂CH₂— | " |
| 5,6-di-Cl | " | " | —CH₂CH₂NHSO₂CH₂CH₂CH₂CH₂— | " |
| 5-SO₂CH₃ | " | " | —CH₂CH₂SO₂NHCH₂CH₂— | " |
| 5-SO₂NH₂ | " | " | —CH₂CH₂N(COCH₃)CH₂CH₂— | " |
| 5-SO₂NHC₂H₅ | " | " | —CH₂CH₂CONHC₂H₄— | " |
| H | " | " | —CH₂CH₂NHCOCH₂— | " |
| " | " | " | —CH₂CH₂N(SO₂C₆H₅)CH₂CH₂— | " |
| " | " | " | —CH₂CH₂SO₂N(CH₃)CH₂CH₂— | " |
| " | " | " | —CH₂CH₂SO₂N(C₆H₅)CH₂CH₂— | " |
| " | " | " | —CH₂CH₂N(SO₂C₆H₁₁)CH₂CH₂— | " |
| " | " | " | —CH₂CH₂N(COCH₃)CH₂CH₂— | " |
| " | " | " | —CH₂CH(CH₂OCH₃)— | " |
| " | " | " | —CH₂CH(Cl)CH₂— | " |
| " | " | " | —CH₂CH₂NHCONHC₂H₄— | " |
| " | " | " | —CH₂CH₂NHCOOCH₂CH₂— | " |
| " | " | " | —CH₂CH₂COOCH₂CH₂ | " |

TABLE II

| R | (R₁)m | R₃ | R₄ | Z | M |
|---|---|---|---|---|---|
| 5-Cl | H | CH₃ | CH₃ | —CH₂CH₂— | K⁺ |
| " | 7-CH₃ | " | " | " | " |
| " | 7-OCH₃ | " | " | " | " |
| " | 7-Cl | " | " | " | " |
| " | 5-CH₃, 8-OCH₃ | " | " | " | " |
| " | 5,8-di-OCH₃ | " | " | " | " |
| " | 5,8-di-CH₃ | " | " | " | " |
| " | 5-Cl, 8-OCH₃ | " | " | " | " |
| " | 8-OCH₃ | " | " | " | " |
| " | 8-OC₂H₅ | H | H | " | " |
| " | 7-CH₃ | " | " | " | " |
| H | 7-NHCOCH₃ | CH₃ | CH₃ | " | Na⁺ |
| " | 7-NHCOH | " | " | " | " |
| " | 7-NHCOCH₂OCH₃ | " | " | " | " |
| " | 7-NHCOCH₂OC₆H₅ | H | CH(CH₃)₂ | " | " |
| " | 7-NHCOCH₂C₆H₅ | " | " | " | " |
| " | 7-NHCOCH₂Cl | " | " | " | " |
| " | 7-NHCOC₆H₅ | " | " | " | " |
| " | 7-NHCOC₆H₁₁ | CH₃ | CH₃ | " | " |
| " | 7-NHCONHC₂H₅ | " | " | " | " |
| " | 7-NHSO₂CH₃ | " | " | " | " |
| " | 7-NHCOCH₂CN | " | " | " | " |
| " | 7-NHCOCH₂OH | " | " | " | " |
| " | 7-NHCOOC₂H₅ | " | " | —CH₂CH₂CH₂— | " |
| " | 7-NHCOCH₂CH₂OCOCH₃ | " | " | " | " |
| " | 8-OC₄H₉-n | H | CH₃ | —CH₂CH₂— | " |
| " | 7-CH₃ | CH₃ | H | " | " |
| " | | " | CH₃ | " | " |
| " | 7-NHCO-(furyl) | | | | |
| 5-Br | 7-OC₂H₅ | " | " | " | " |
| 5-I | 7-OC₄H₉-n | " | " | " | " |
| 6-CH₃ | 7-CH₃ | " | H | " | " |
| 6-OCH₃ | " | " | " | " | " |

TABLE II-continued

| R | $(R_1)m$ | $R_3$ | $R_4$ | Z | M |
|---|---|---|---|---|---|
| 5,6-di-Cl | " | " | " | —CH$_2$CH$_2$CH$_2$CH$_2$— | " |
| 5-SO$_2$CH$_3$ | " | " | " | —CH$_2$CH$_2$— | " |
| 5-SO$_2$NH$_2$ | " | " | " | " | " |
| 5-SO$_2$NHCH$_3$ | " | " | " | " | " |
| H | " | " | " | —CH$_2$CH$_2$SO$_2$CH$_2$CH$_2$— | K$^+$ |
| " | " | " | " | —CH$_2$CH$_2$OCH$_2$CH$_2$— | " |
| " | " | " | " | —CH$_2$CH$_2$SCH$_2$CH$_2$— | " |
| " | " | " | " | —CH$_2$CH(C$_6$H$_5$)— | " |
| " | " | " | " | —CH$_2$CH(CH$_3$)— | " |
| " | " | " | " | —CH$_2$CH(OH)CH$_2$— | " |
| " | " | " | " | —CH$_2$CH(Cl)CH$_2$— | " |
| " | " | " | " | —CH$_2$CH(CH$_2$OCH$_2$CH$_3$)— | " |
| " | " | " | " | —CH$_2$CH(CH$_2$OC$_6$H$_5$)— | " |
| " | " | " | " | —CH$_2$CH$_2$N(SO$_2$CH$_3$)CH$_2$CH$_2$— | " |
| " | " | " | " | —CH$_2$CH$_2$CH$_2$NHSO$_2$CH$_2$CH$_2$— | " |
| " | " | " | " | —CH$_2$CH$_2$SO$_2$NHCH$_2$CH$_2$— | " |
| " | " | " | " | —CH$_2$CH$_2$NHCOCH$_2$— | " |
| " | " | " | " | —CH$_2$CH$_2$NHCOOCH$_2$CH$_2$— | " |
| " | " | " | " | —CH$_2$CH$_2$COOCH$_2$CH$_2$— | " |
| " | " | " | " | —CH$_2$CH$_2$CONHC$_2$H$_4$— | " |
| " | " | " | " | —CH$_2$CH$_2$NHCONHC$_2$H$_4$— | " |
| " | " | " | " | —CH$_2$CH$_2$N(SO$_2$C$_6$H$_5$)CH$_2$CH$_2$— | " |
| " | " | " | " | —CH$_2$CH$_2$N(COCH$_3$)CH$_2$CH$_2$— | " |
| " | " | " | " | —CH$_2$CH$_2$SO$_2$N(C$_6$H$_5$)CH$_2$CH$_2$— | " |
| " | " | " | " | —CH$_2$CH$_2$SO$_2$N(CH$_3$)CH$_2$CH$_2$— | " |

TABLE III

| R | $(R_1)n$ | $R_3$ | Z | M |
|---|---|---|---|---|
| 5-Cl | 6-CH$_3$ | H | —CH$_2$CH$_2$— | K$^+$ |
| " | H | H | " | " |
| " | " | CH$_3$ | " | " |
| " | 6-CH$_3$ | " | " | " |
| " | " | " | —CH$_c$H$_2$CH$_2$CH$_2$— | " |
| " | 6-OCH$_3$ | " | " | " |
| " | " | " | —CH$_2$CH$_2$— | " |
| " | 6-CH$_3$ | " | —CH$_2$CH$_2$OCH$_2$CH$_2$— | " |
| " | " | " | —CH$_2$CH$_2$SO$_2$CH$_2$CH$_2$— | " |
| " | " | " | —CH$_2$CH$_2$SCH$_2$CH$_2$— | " |
| " | " | " | —CH$_2$CH(CH$_3$)— | " |
| H | " | " | —CH$_2$CH(C$_6$H$_5$)— | " |
| " | 6-OC$_2$H$_5$ | " | —CH$_2$CH$_2$— | " |
| " | 6-NHCOCH$_3$ | " | " | Na$^+$ |
| " | 6-NHCOH | " | " | " |
| " | 6-NHCOCH$_2$CH$_2$OCH$_3$ | " | " | " |
| " | 6-NHCOCH$_2$Cl | " | " | " |
| " | 6-NHCOCH$_2$CN | " | " | " |
| " | 6-NHCOCH$_2$CONH$_2$ | " | " | " |
| " | 6-NHCOCH$_2$OC$_6$H$_5$ | " | " | " |
| " | 6-NHCOOC$_2$H$_5$ | " | " | " |
| " | 6-NHCONHC$_2$H$_5$ | " | " | " |
| " | 6-NHCOC$_6$H$_5$ | " | " | " |
| " | 6-NHCOC$_6$H$_{11}$ | " | " | " |
| " | 6-NHSO$_2$CH$_3$ | " | " | " |
| " | 6-NHCOCH$_2$CH$_2$OCOCH$_3$ | " | " | " |

TABLE III-continued

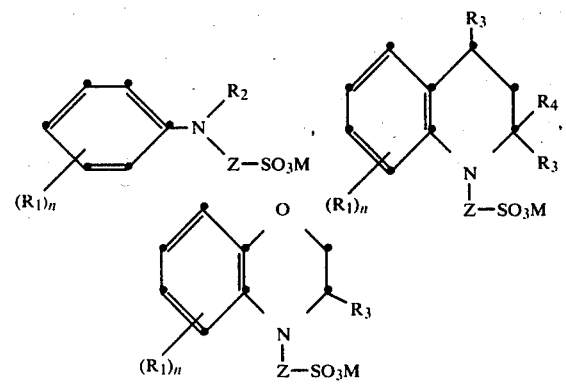

| R | (R₁)ₙ | R₃ | Z | M |
|---|---|---|---|---|
| " | 6-NHCO-[furan] | " | " | " |
| " | 6-NHCOCH₂CH₂CH₂OH | " | " | " |
| 5-Br | 6-CH₃ | " | —CH₂CH₂CH₂— | " |
| 5-I | " | " | —CH₂CH₂— | " |
| 6-CH₃ | " | " | " | " |
| 6-OCH₃ | " | " | " | " |
| 5,6-di-Cl | " | " | " | " |
| 5-SO₂CH₃ | " | " | " | " |
| 5-SO₂NH₂ | " | " | " | " |
| 5-SO₂NHC₄H₉-n | " | " | " | " |
| H | " | H | —CH₂CH(CH₃)— | " |
| H | " | CH₃ | —CH₂CH₂N(SO₂CH₃)CH₂CH₂— | K⁺ |
| " | " | " | —CH₂CH₂SO₂NHCH₂CH₂— | " |
| " | " | " | —CH₂CH₂SO₂N(CH₃)CH₂CH₂CH₂— | " |
| " | " | " | —CH₂CH₂SO₂N(C₆H₅)CH₂CH₂— | " |
| " | " | " | —CH₂CH₂SO₂N(C₆H₁₁)CH₂CH₂— | " |
| " | " | " | —CH₂CH₂CH₂CH₂N(SO₂CH₃)CH₂CH₂— | " |
| " | " | " | —CH₂CH₂N(SO₂C₆H₄-p-CH₃)—CH₂CH₂— | " |
| " | " | " | —CH₂CH₂N(SO₂C₆H₁₁)CH₂CH₂— | " |
| " | " | " | —CH₂CH(Cl)CH₂— | " |
| " | " | " | —CH₂CH(OH)CH₂— | " |
| " | " | " | —CH₂CH(CH₂OCH₃)— | " |
| " | " | " | —CH₂CH(CH₂OC₆H₅)— | " |
| " | " | " | —CH₂CH(OCOCH₃)CH₂— | " |
| " | " | " | —CH₂CH₂NHCOCH₂— | " |
| " | " | " | —CH₂CH₂CONHC₂H₄— | " |
| " | " | " | —CH₂CH₂NHCOOCH₂CH₂— | " |
| " | " | " | —CH₂CH₂COOCH₂CH₂— | " |
| " | " | " | —CH₂CH₂NHCONHCH₂CH₂— | " |
| " | " | " | —CH₂CH₂N(COCH₃)CH₂CH₂— | " |
| " | " | " | —CH₂CH₂N(COC₆H₅)CH₂CH₂— | " |

The invention has been described in detail with particular reference to preferred embodiments thereof, but it will be understood that variations and modifications can be effected within the spirit and scope of the invention.

We claim:

1. A dye of the formula:

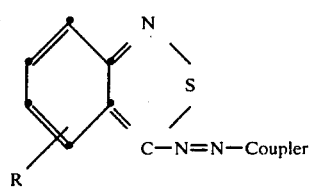

wherein the Coupler is of the formulae

[structural formulae showing three coupler structures with R₂, R₃, R₄, (R₁)ₙ, Z—SO₃M substituents]

wherein R may be hydrogen or one to three substituents selected from lower alkyl, lower alkoxy, chlorine, bromine, iodine, lower alkylsulfonyl, sulfamoyl, and sulfamoyl substituted with lower alkyl; R₁ is selected from hydrogen, lower alkyl, aryl, alkylamino, 2-furyl, halogen, lower alkoxy, aryloxy, —NHCO—R₅ and —NHSO₂—R₅ wherein R₅ is selected from lower alkyl which may be substituted with hydroxy, lower alkoxy, cyano, aryloxy, aryl, halogen, cycloalkyl, lower alkylcarbonyloxy, or carbamoyl; $R_2$ is selected from hydrogen, aryl, cycloalkyl, and lower alkyl which may be substituted with alkoxy, alkoxyalkoxy, aryl, cycloalkyl, lower alkylcycloalkyl, 2-furyl, $NHCOR_5$, $NHSO_2R_5$, aryloxy, alkylcarbonyl, carbamoyl, lower alkyl substituted carbamoyl, cyano, alkanoyloxy, halogen, alkoxycarbonyl, succinimido, glutarimido, phthalimido, 2-pyrrolidono, sulfamoyl, lower alkyl substituted sulfamoyl, lower alkylsulfonamido, $NHSO_2$-aryl, NHCOO-alkyl, NHCONH-alkyl, formamido, alkylsulfonyl, arylsulfonyl, alkylthio, arylthio or $SO_3M$; $R_2$ may in conjunction with $R_1$ form a 1,2,3,4-tetrahydroquinoline or benzomorpholine derivative; n is 0, 1 or 2; M is $Na^+$, $K^+$, $NH_4^+$, or $H^+$; $R_3$ and $R_4$ are each selected from hydrogen or lower alkyl; Z is selected from straight or branched chain lower alkylene, lower alkylene substituted with aryl, aryloxy, alkoxy, halogen, aryloxy or $SO_3M$, $-CH_2(CH_2)_m-X-CH_2(CH_2)_p$, where m is 1, 2, or 3, p is 0, 1, 2, or 3, and X is O, S, $SO_2$, $-SO_2NH-$, $-SO_2\overset{|}{N}-$alkyl, $-\overset{|}{N}-SO_2-$alkyl, $-\overset{|}{N}-SO_2-$aryl, $-\overset{|}{N}-SO_2-$cyclohexyl, $-\overset{|}{N}CO-$alkyl, $-NHCO-$, $-NHCOO-$, $-\overset{alkyl}{\underset{|}{N}}-CO-$, $-\overset{aryl}{\underset{|}{N}}-SO_2-$, or $-NH\overset{O}{\overset{||}{C}}NH-$;

and the various aryl groups may be substituted with lower alkyl, lower alkoxy, or halogen.

2. A dye according to claim 1 wherein R is selected from H, lower alkyl, lower alkoxy and halogen; $R_1$ is selected from hydrogen, lower alkyl, and lower alkoxy; $R_2$ is selected from hydrogen or lower alkyl; and Z is straight or branched chain lower alkylene.

3. The dye according to claim 1 having the formula

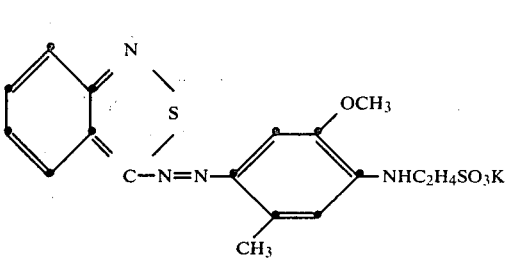

4. The dye according to claim 1 having the formula

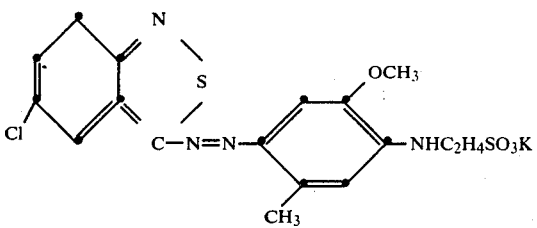

5. The dye according to claim 1 having the formula

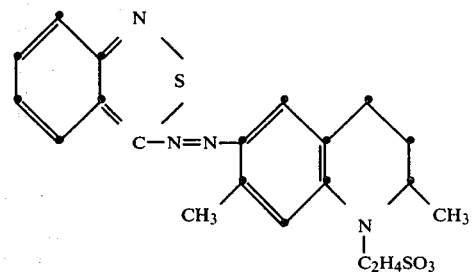

6. The dye according to claim 1 having the formula

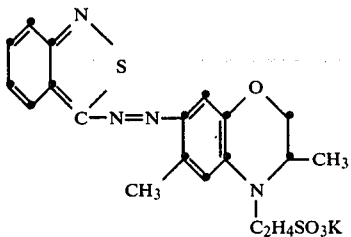

* * * * *

UNITED STATES PATENT AND TRADEMARK OFFICE
CERTIFICATE OF CORRECTION

PATENT NO. : 4,265,812
DATED : May 5, 1981
INVENTOR(S) : Weaver et al

It is certified that error appears in the above—identified patent and that said Letters Patent is hereby corrected as shown below:

Column 16, lines 13-23, the structure of claim 4 should read

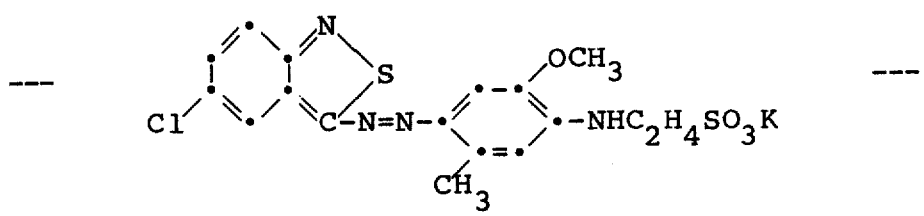

Column 16, lines 25-36, the structure of claim 5 should read

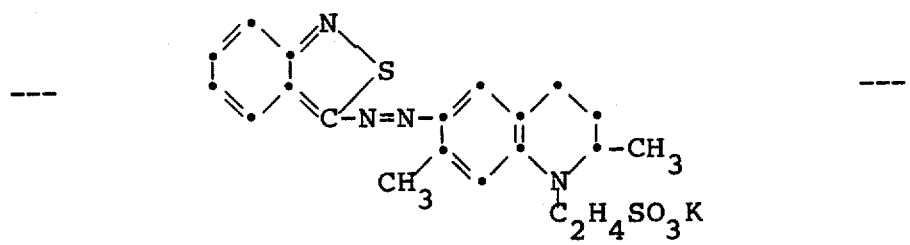

Signed and Sealed this

Tenth Day of August 1982

[SEAL]

Attest:

GERALD J. MOSSINGHOFF

Attesting Officer    Commissioner of Patents and Trademarks